(12) United States Patent
Seimori (10) Patent No.: US 11,016,069 B2
(45) Date of Patent: May 25, 2021

(54) APPARATUS AND METHOD FOR EVALUATING RESPONSE TIME OF GAS SENSOR

(71) Applicant: NGK INSULATORS, LTD., Nagoya (JP)

(72) Inventor: Tomoya Seimori, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 183 days.

(21) Appl. No.: 16/351,556

(22) Filed: Mar. 13, 2019

(65) Prior Publication Data
US 2019/0285597 A1    Sep. 19, 2019

(30) Foreign Application Priority Data

Mar. 15, 2018  (JP) .............................. JP2018-048305

(51) Int. Cl.
*G01N 33/00* (2006.01)

(52) U.S. Cl.
CPC ....... *G01N 33/007* (2013.01); *G01N 33/0037* (2013.01); *G01N 33/0054* (2013.01); *G01N 2033/0072* (2013.01)

(58) Field of Classification Search
CPC ....... G01N 2033/0072; G01N 33/0037; G01N 33/0054; G01N 33/007
See application file for complete search history.

(56) References Cited

U.S. PATENT DOCUMENTS

| | | | | | |
|---|---|---|---|---|---|
| 3,762,878 | A | * | 10/1973 | Villalobos ......... | G01N 33/0024 436/143 |
| 4,825,683 | A | * | 5/1989 | Takami ............. | G01N 33/0006 73/1.06 |
| 5,520,858 | A | * | 5/1996 | Yamaguchi ......... | B01D 1/0076 261/122.1 |
| 5,531,218 | A | * | 7/1996 | Krebs ................... | A61M 16/12 128/203.12 |
| 5,565,180 | A | * | 10/1996 | Spink .................... | B01D 53/34 423/220 |

(Continued)

FOREIGN PATENT DOCUMENTS

| | | |
|---|---|---|
| EP | 0 273 765 A2 | 7/1988 |
| FR | 2 844 880 A1 | 3/2004 |

(Continued)

OTHER PUBLICATIONS

Extended European Search Report received in corresponding European Application No. 19160195.4 dated Sep. 6, 2019.

*Primary Examiner* — Francis C Gray
(74) *Attorney, Agent, or Firm* — Mattingly & Malur, PC (57) ABSTRACT

An apparatus for evaluating a response time of gas sensors includes: a pipe; a first gas supplier for supplying a first gas to the pipe; a second gas adding machine for adding a second gas to the first gas in the pipe; and gas sensors for detecting components in a mixed gas of the first gas and the second gas, each of the gas sensors being attached to the pipe on a downstream side of an addition position of the second gas in a flow direction of the first gas. The second gas adding machine includes: a supply source of the second gas; a connecting pipe for connecting the supply source to the pipe; and a connecting pipe on-off valve for opening and closing the connecting pipe.

12 Claims, 4 Drawing Sheets

(56) References Cited

U.S. PATENT DOCUMENTS

| | | | |
|---|---|---|---|
| 7,722,749 B2 | | 5/2010 | Wang et al. |
| 2011/0011152 A1 | | 1/2011 | Ito et al. |
| 2014/0123744 A1 † | | 5/2014 | Takamiya |
| 2016/0348561 A1 * | | 12/2016 | Higashi .................. G01N 21/15 |

FOREIGN PATENT DOCUMENTS

| JP | 2011-039041 A | | 2/2011 |
|---|---|---|---|
| JP | 2016-090484 A | | 5/2016 |
| JP | 2016-90484 A | † | 5/2016 |
| KR | 2016-0000625 A | | 1/2016 |

\* cited by examiner
† cited by third party

APPARATUS AND METHOD FOR EVALUATING RESPONSE TIME OF GAS SENSOR

CROSS-REFERENCE TO RELATED APPLICATION

The present application claims priority from Japanese application JP 2018-048305, filed on Mar. 15, 2018, the contents of which is hereby incorporated by reference into this application.

TECHNICAL FIELD

The present invention relates to a gas sensor response time evaluating apparatus and method for evaluating a response time of gas sensors.

BACKGROUND ART

As a gas sensor evaluation apparatus of this type which has been conventionally used, for example, the configurations shown in Patent Documents 1 and 2 below can be mentioned. Patent Document 1 discloses that a plurality of gases whose flow rates are controlled by a mass flow controller are mixed by means of a mixing device to generate a mixed gas. The mixed gas is supplied to a gas sensor(s) to be tested. In this configuration, the flow rate of each gas is adjusted by the mass flow controller to change a mixing ratio of each gas, whereby a response characteristic and the like of the gas sensor(s) can be evaluated.

Patent Document 2 discloses that a tip portion of a gas sensor attached to a chamber is covered with a cap. When the tip of the gas sensor is covered with the cap, an atmosphere in the cap is different from that in the chamber. By releasing the covering with the cap, the atmosphere around the gas sensor is instantly switched. By switching the atmosphere around the gas sensor, the response characteristic and the like of the gas sensor can be evaluated.

CITATION LIST

Patent Literatures

Patent Document 1: Japanese Patent Application Publication No. 2011-39041 A
Patent Document 2: Japanese Patent Application Publication No. 2016-90484 A

SUMMARY OF INVENTION

Technical Problem

In the configuration described in Patent Document 1 as described above, the flow rates of the gases are adjusted by the mass flow controller, so that the mixing ratio of the gases cannot be instantaneously switched due to control delay of the mass flow controller. Therefore, it is difficult to know accurately a time point when the mixing ratio of the gases is actually changed, so that evaluation accuracy of characteristics such as the response characteristic of the gas sensor is deteriorated.

On the other hand, in the configuration disclosed in Patent Document 2 as described above, the atmosphere around the gas sensor can be instantaneously switched by releasing the covering with the cap. However, when the cap is used, the gas is suddenly switched from a substantially windless state. Such sudden switching of the gas from the windless state does not occur in an actual use environment of the gas sensor, and the evaluation test using the cap deviates from the actual environment.

The present invention has been made to solve the above problems. An object of the present invention is to provide an apparatus for evaluating a response time of gas sensors, which can improve evaluation accuracy of a response characteristic time of the gas sensors while simulating the actual use environment of the gas sensors. Another object of the present invention is to provide a method for evaluating a response time of gas sensors, which can improve evaluation accuracy of a response characteristic time of the gas sensors while simulating the actual use environment of the gas sensors.

Solution to Problem

In one aspect, an apparatus for evaluating a response time of gas sensors according to the present invention comprises a pipe; a first gas supplier for supplying a first gas to the pipe; a second gas adding machine for adding a second gas to the first gas in the pipe; and gas sensors for detecting components in a mixed gas of the first gas and the second gas, each of the gas sensor being attached to the pipe on a downstream side of an addition position of the second gas in a flow direction of the first gas, wherein the second gas adding machine comprises: a supply source of the second gas; a connecting pipe for connecting the supply source to the pipe; and a connecting pipe on-off valve for opening and closing the connecting pipe.

In another aspect, a method for evaluating a response time of gas sensors according to the present invention relates a gas sensor response time evaluating method for evaluating the response time of the gas sensors using the response time evaluation apparatus as described above, comprising an attachment step of attaching the gas sensors to the pipe; a first gas supply start step of starting supply of the first gas to the pipe by the first gas supplier; an addition step of opening the connecting pipe by the connecting pipe on-off valve and adding the second gas to the first gas in the pipe; and a time difference acquisition step of acquiring a time difference between a time point when the connecting pipe is opened by the connecting pipe on-off valve and a time point when the gas sensors detect the components in the mixed gas of the first and second gases.

Advantageous Effects of Invention

According to one embodiment of the apparatus and method for evaluating the response time of the gas sensors of the present invention, the second gas adding machine includes the supply source of the second gas, the connecting pipe for connecting the supply source to the pipe and the connecting pipe on-off valve for opening and closing the connecting pipe, so that the evaluation accuracy of the response characteristic time of the gas sensors can be improved while simulating the actual use environment of the gas sensors.

DESCRIPTION OF THE PREFERRED EMBODIMENTS

Hereinafter, embodiments for carrying out the present invention will be described with reference to the drawings. It should be noted that the present invention is not limited to the embodiments, and it can be embodied by modifying elements without departing from the spirit of the present invention. Further, some elements may be deleted from all elements shown in the embodiments.

Figure 1:
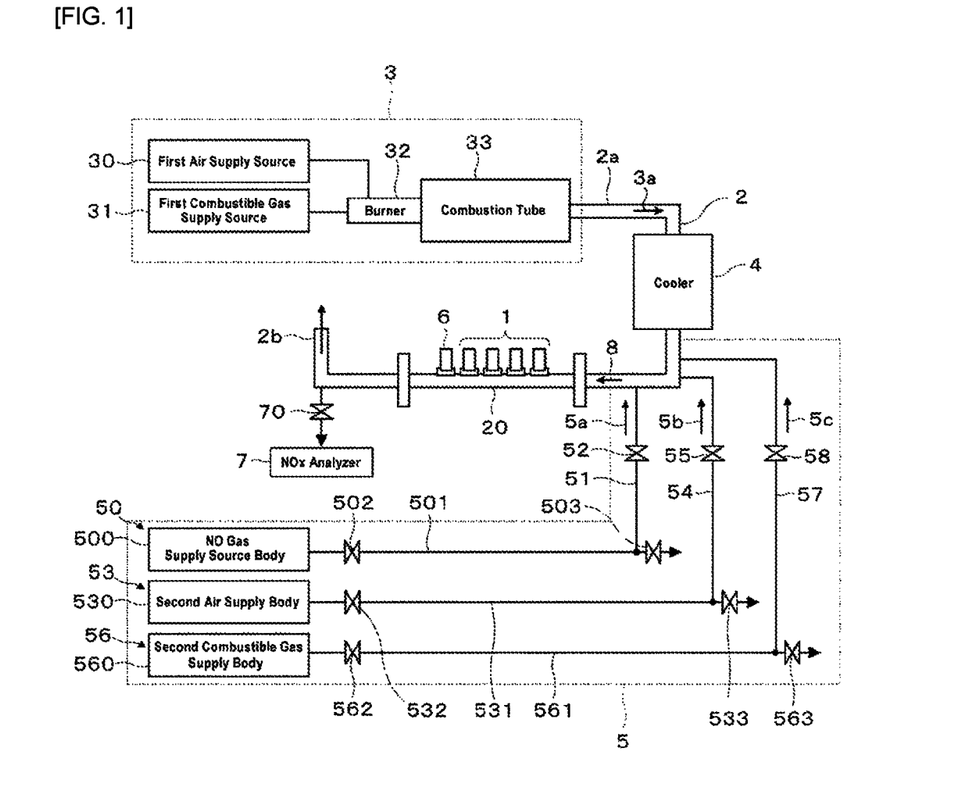
FIG. 1 is an explanatory view showing a configuration of a response time evaluation apparatus for gas sensors according to an embodiment of the present invention.

FIG. 1 is an explanatory view showing a configuration of a response time evaluation apparatus for gas sensors according to an embodiment of the present invention. The response time evaluation device according to the present embodiment shown in FIG. 1 is an apparatus for evaluating the response time of a plurality of gas sensors 1. Any number of the gas sensors 1 for evaluating the response time may be used and the number may be one. Each of the gas sensor 1 of the present embodiment is capable of detecting at least one component of a gas to be measured. The gas to be measured may be an exhaust gas of a vehicle on which an engine is mounted. Examples of the components to be detected by the gas sensors 1 include NOx, ammonia, oxygen and the like. The present embodiment will describe the gas sensors 1 as sensors for detecting NOx and oxygen.

The response time of each gas sensor 1 in the present embodiment includes a time required for a change of an output signal of the gas sensor 1 relative to a change of the component to be detected. The time required for the change of the output signal of the gas sensor 1 can be a time from a time point when the output signal of the gas sensor 1 reaches a predetermined first threshold value to a time point when the output signal reaches a second threshold value which is at a higher level than the first threshold value, when the output signal of the gas sensor is increased. The first and second threshold values are set depending on the change of the components to be detected. More particularly, the first threshold value is set depending on an initial value relating to the change of the component to be detected, and the second threshold value is set depending on the value obtained by adding a change amount of the component to be detected to the initial value. That is, a difference between the first and second threshold values corresponds to the change amount of the component to be detected. Further, the first threshold value is not necessarily zero. The change of the component to be detected includes a change of a component concentration. Further, the time required for the change of the output signal of the gas sensor 1 is can be a time from a time point when the output signal of the gas sensor 1 reaches the second threshold to a time point when the output signal reaches the first threshold, when the output signal of the gas sensor 1 is decreased.

As shown in FIG. 1, the response time evaluation apparatus according to the present embodiment includes a pipe 2; a first gas supplier 3; a cooler 4; a second gas adding machine 5; and an air-fuel ratio meter 6 and a NOx analyzer 7.

<Regarding Pipe 2>

The pipe 2 according to the present embodiment is a tubular body having a flow path therein. One end 2a of the pipe 2 is connected to the first gas supplier 3, and other end 2b of the pipe 2 is opened to the atmosphere. The pipe 2 according to the present embodiment includes a chamber 20 to which gas sensors 1 and the air-fuel ratio meter 6 are attached.

<Regarding First Gas Supplier 3>

The first gas supplier 3 according to the present embodiment is a device for allowing a first gas 3a to flow through the pipe 2. The first gas supplier 3 according to the present embodiment includes: a first air supply source 30; a first combustible gas supply source 31; a burner 32; and a combustion tube 33.

The first air supply source 30 supplies air to the burner 32 and the first combustible gas supply source 31 supplies a combustible gas to the burner 32. Examples of the combustible gas that can be used include a liquefied natural gas (LNG) and the like. Flow rates of the air and the combustible gas supplied to the burner 32 are adjusted so as to have a predetermined air-fuel ratio. An air ratio A (an amount of air supplied to the burner 32/an amount of air required for an ideal air-fuel ratio) can be in a range of 0.8 or more and 0.9 or less, for example. When the air ratio A is in the range of 0.8 or more and 0.9 or less, the first gas 3a contains about 100 ppm by volume of NOx.

The burner 32 burns the air from the first air supply source 30 and the combustible gas from the first combustible gas supply source 31 to generate a combustion gas. That is, the first gas 3a according to the present embodiment is a combustion gas in which the combustible gas has been burned. The combustion pipe 33 is a tubular body for covering a periphery of the tip of the burner 32 and for guiding the first gas 3a from the burner 32 to the one end 2a of the pipe 2.

<Regarding Cooler 4>

The cooler 4 according to the present embodiment is a device for cooling the first gas 3a. A temperature of the first gas 3a can be decreased, for example, from about 800° C. to about 350° C., by the cooler 4. Examples of the cooler 4 that can be used include a water cooling jacket including a water cooling pipe wound around the pipe 2 and the like.

<Regarding Second Gas Adding Machine 5>

The second gas adding machine 5 according to the present embodiment is a device for adding a second gas to the first gas 3a in the pipe 2. The second gas is a gas for adjusting the component of the first gas 3a. In other words, the first gas 3a is steadily generated, and the component of the gas supplied to the gas sensors 1 can be changed by the second gas.

An addition position of the second gas is preferably closer to the gas sensors 1, because an effect of the addition of the second gas can be more quickly produced at the position of the gas sensors 1. In the present embodiment, a distance between the addition position of the second gas and the gas sensors 1 is shorter than a distance between the addition position of the second gas and the first gas supplier 3. These distances are those along the pipe 2. The distance between the addition position of the second gas and the gas sensors 1 is preferably 20% or less of the distance between the addition position of the second gas and the first gas supplier 3, and more preferably 10% of that distance. Further, in the present embodiment, the addition position of the second gas is arranged on a downstream side of the cooler 4 in a flow direction of the first gas 3a.

The second gas adding machine 5 according to the present embodiment adds, as the second gas, at least one of a plurality of gases to the first gas 3a. More particularly, the second gas adding machine 5 according to the present embodiment adds, as the second gas, at least one of a NO gas 5a (a nitrogen monoxide gas), air 5b and a combustible gas 5c to the first gas 3a in the pipe 2. The NO gas 5a can be used to evaluate a response time of a NO output for the gas sensor 1. The air 5b and the combustible gas 5c can be used to evaluate a response time of an oxygen output for the gas sensor 1. The air 5b can be added to create a state of excessive oxygen relative to the ideal air-fuel ratio, and the combustible gas 5c can be added to create a state of excessive fuel relative to the ideal air-fuel ratio.

<Regarding Configuration of Second Gas Adding Machine 5>

The second gas adding machine 5 according to the embodiment includes: an NO gas supply source 50; a first connecting pipe 51; a first connecting pipe on-off valve 52; a second air supply source 53; a second connecting pipe 54; a second connecting pipe on-off valve 55; a second combustible gas supply source 56; a third connecting pipe 57; and a third connecting pipe on-off valve 58.

<Regarding NO Gas Supply Source 50, First Connecting Pipe 51, and First Connecting Pipe On-Off Valve 52>

The NO gas supply source 50 is configured to supply the NO gas 5a. The first connecting pipe 51 is a pipe for connecting the NO gas supply source 50 to the pipe 2. The first connecting pipe on-off valve 52 is a valve for opening and closing the first connecting pipe 51. When the NO gas supply source 50 is in a state being capable of supplying the NO gas 5a, the NO gas 5a is added to the first gas 3a in the pipe 2 through the first connection tube 51, by opening the first connecting pipe on-off valve 52. A concentration of the NO gas 5a added may be, for example, 0 ppm by volume or more and 500 ppm by volume or less.

The NO gas supply source 50 according to the present embodiment includes an NO gas supply source body 500; a first supply pipe 501; a first supply control valve 502; and a first supply pipe on-off valve 503.

The NO gas supply source body 500 is configured to have a supply capability of the NO gas 5a such as a gas cylinder in which the NO gas 5a is stored, for example. The first supply pipe 501 is a pipe whose one end is connected to the NO gas supply source body 500. The first connecting pipe 51 is connected to the first supply pipe 501, and the NO gas 5a from the NO gas supply source body 500 is supplied to the first connecting pipe 51 through the first supply pipe 501. The other end of the first supply pipe 501 according to the present embodiment is opened to the atmosphere. The other end of the first supply pipe 501 may be connected to a tank or piping system having a large capacity to such an extent that it can be regarded as the atmosphere.

The first supply control valve 502 is a valve for opening and closing the first supply pipe 501 on an upstream side of the connection position of the first connecting pipe 51 to the first supply pipe 501 in the flow direction of the NO gas 5a. The first supply pipe on-off valve 503 is a valve for opening and closing the first supply pipe 501 on a downstream side of the connection position of the first connecting pipe 51 to the first supply pipe 501 in the flow direction of the NO gas 5a. When the first supply control valve 502 is opened, the NO gas supply source 50 according to the present embodiment will be in a state being capable of supplying the NO gas 5a. Further, in the NO gas supply source 50 according to the present embodiment, the first supply control valve 502 and the first supply pipe on-off valve 503 are opened, whereby even if the connecting pipe 51 is closed by the connecting pipe on-off valve 52, the flow of the NO gas 5a can be formed in the first supply pipe 501. When the connecting pipe on-off valve 52 is opened, the first supply pipe on-off valve 503 is preferably closed.

<Regarding Second Air Supply Source 53, Second Connecting Pipe 54, and Second Connecting Pipe On-Off Valve 55>

The second air supply source 53, the second connecting pipe 54, and the second connecting pipe on-off valve 55 are the same as the NO gas supply source 50, the first connecting pipe 51 and the first connecting pipe on-off valve 52, respectively, with the exception that the air 5b is supplied in place of the NO gas 5a.

The second air supply source 53 is configured to supply the air 5b. The second connecting pipe 54 is a pipe for connecting the second air supply source 53 to the pipe 2. The second connecting pipe on-off valve 55 is a valve for opening and closing the second connecting pipe 54. When the second air supply source 53 is in a state being capable of supplying the air 5b, the air 5b is added to the first gas 3a in the pipe 2 through the second connecting pipe 54, by opening the second connecting pipe on-off valve 55.

The second air supply source 53 according to the present embodiment includes: a second air supply body 530; a second supply pipe 531; a second supply control valve 532; and a second supply pipe on-off valve 533.

The second air supply source body 530 is configured to have a supply capability of the air 5b such as a gas cylinder in which the air 5b is stored, for example. The second supply pipe 531 is a pipe whose one end is connected to the second air supply source body 530. The second connecting pipe 54 is connected to the second supply pipe 531, and the air 5b from the second air supply source body 530 is supplied to the second connecting pipe 54 through the second supply pipe 531. The other end of the second supply pipe 531 according to the present embodiment is opened to the atmosphere. The other end of the second supply pipe 531 may be connected to a tank or piping system having a large capacity to such an extent that it can be regarded as the atmosphere.

The second supply control valve 532 is a valve for opening and closing the second supply pipe 531 on an upstream side of the connection position of the second connecting pipe 54 to the second supply pipe 531 in the flow direction of the air 5b. The second supply pipe on-off valve 533 is a valve for opening and closing the second supply pipe 531 on a downstream side of the connecting position of the second connecting pipe 54 to the second supply pipe 531 in the flow direction of the air 5b. When the second supply control valve 532 is opened, the second air supply source 53 according to the present embodiment will be in a state being capable of supplying the air 5b. Further, in the second air supply source 53 according to the present embodiment, the second supply control valve 532 and the second supply pipe on-off valve 533 are opened, whereby even if the connecting pipe 54 is closed by the connecting pipe on-off valve 55, the flow of the air 5b can be formed in the second supply pipe 531. When the connecting pipe on-off valve 55 is opened, the second supply pipe on-off valve 533 is preferably closed.

Regarding Second Fuel Gas Supply Source 56, Third Connecting Pipe 57 and Third Connecting Pipe On-Off Valve 58

The second combustible gas supply source 56, the third connecting pipe 57, and the third connecting pipe on-off valve 58 are the same as the NO gas supply source 50, the first connecting pipe 51 and the first connecting pipe on-off valve 52, respectively, with the exception that the combustible gas 5c is supplied in place of the NO gas 5a.

The second combustible gas supply source 56 is configured to supply the combustible gas 5c. The third connecting pipe 57 is a pipe for connecting the second combustible gas supply source 56 to the pipe 2. The third connecting pipe on-off valve 58 is a valve for opening and closing the third connecting pipe 57. When the second combustible gas supply source 56 is in a state being capable of supplying the combustible gas 5c, the combustible gas 5c is added to the first gas 3a in the pipe 2 through the third connecting pipe 57 by opening the third connecting pipe on-off valve 58.

The second combustible gas supply source 56 according to the present embodiment includes: a second combustible gas supply body 560; a third supply pipe 561; a third supply control valve 562; and a third supply pipe on-off valve 563.

The second combustible supply source body 560 is configured to have a supply capability of the combustible gas 5c such as a gas cylinder in which the combustible gas 5c is stored, for example. The third supply pipe 561 is a pipe whose one end is connected to the second combustible gas supply source body 560. The third connecting pipe 57 is connected to the third supply pipe 561, and the combustible gas 5c from the second combustible gas supply source body 560 is supplied to the third connecting pipe 57 through the third supply pipe 561. The other end of the third supply pipe 561 according to the present embodiment is opened to the atmosphere. The other end of the third supply pipe 561 may be connected to a tank or piping system having a large capacity to such an extent that it can be regarded as the atmosphere.

The third supply control valve 562 is a valve for opening and closing the third supply pipe 561 on an upstream side of the connection position of the third connecting pipe 57 to the third supply pipe 561 in the flow direction of the combustible gas 5c. The third supply pipe on-off valve 563 is a valve for opening and closing the third supply pipe 561 on a downstream side of the connection position of the third connecting pipe 57 to the third supply pipe 561 in the flow direction of the combustible gas 5c. When the third supply control valve 562 is opened, the second combustible gas supply source 56 according to the present embodiment will be in a state being capable of supplying the combustible gas 5c. Further, in the second combustible gas supply source 56 according to the present embodiment, the third supply control valve 562 and the third supply pipe on-off valve 563 are opened, whereby even if the connecting pipe 57 is closed by the connecting pipe on-off valve 58, the flow of the combustible gas 5c can be formed in the third supply pipe 561. When the connecting pipe on-off valve 58 is opened, the third supply pipe on-off valve 563 is preferably closed.

Although each of the first to third connecting pipe on-off valves 52, 55, 58, and the first to third supply control valves 502, 532, 562, and the first to third supply pipe on-off valves 503, 533, 563 has any configuration, it is preferable that these valves are electrically driven valves. The electrically driven valve includes a motor-operated valve and an electromagnetic valve (a solenoid valve), and is a valve that can control the opening and closing by an electric signal. The motor-operated valve is a valve whose valve body is driven by a motor. The electromagnetic valve is a valve whose valve body is driven by a solenoid actuator. When these valves are the electrically driven valves, the timing of opening and closing of these valves can be more accurately acquired. More preferably, these valves are the electromagnetic valves. When these valves are the electromagnetic valves, a time difference between the opening/closing control by the electric signal and the actual opening/closing is small, and the timing of opening/closing of these valves can be more accurately acquired.

<Regarding Chamber 20, Gas Sensor 1 and Air-Fuel Ratio Meter 6>

The chamber 20 to which the gas sensors 1 and the air-fuel ratio meter 6 are attached is disposed on a downstream side of the addition position of the second gas in the flow direction of the first gas 3a. Each gas sensor 1 according to the present embodiment can detect components in the mixed gas 8 of the first and second gases. More particularly, each gas sensor 1 can detect changes of NOx and oxygen concentrations in the mixed gas 8. The air-fuel ratio meter 6 can measure an air-fuel ratio of the mixed gas 8 of the first and second gases. By measuring the air-fuel ratio, amounts of the air 5b and the combustible gas 5c introduced can be monitored. Outputs of each gas sensor 1 and the air-fuel ratio meter 6 can be stored in a storage device (not shown) and can be displayed on a display (not shown).

<Regarding NOx Analyzer 7>

The NOx analyzer 7 is connected to the pipe 2 via an analyzer on-off valve 70 on a downstream side of the chamber 20 in the flow direction of the first gas 3a. When the analyzer on-off valve 70 is opened, the mixed gas 8 of the first and second gases is introduced into the NOx analyzer 7. The NOx analyzer 7 can analyze NOx in the mixed gas 8 of the first and second gases. More particularly, the NOx analyzer 7 can detect a ratio (ppm by volume) of NOx in the mixed gas 8 of the first and second gases. By detecting the ratio of NOx, an amount of the NO gas 5a introduced can be monitored.

Figure 2:
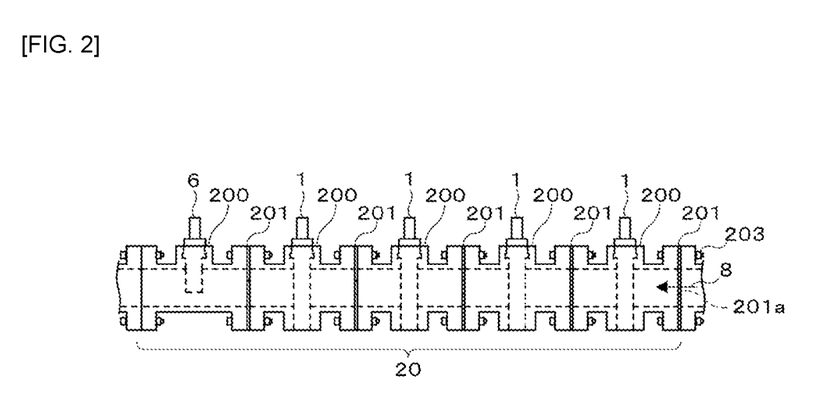
FIG. 2 is a side view showing the chamber in FIG. 1 in more detail.
Figure 3:
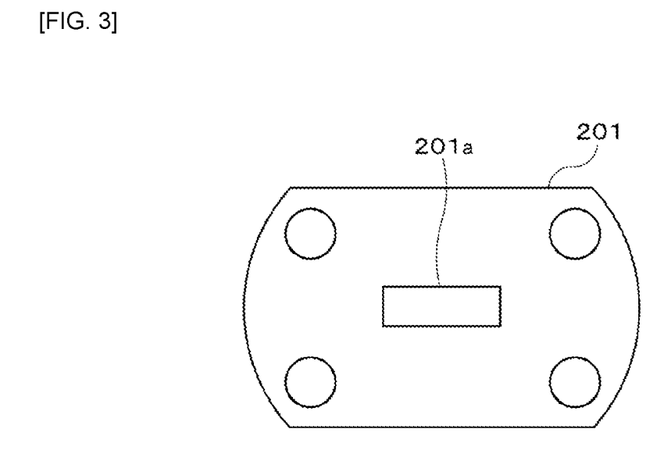
FIG. 3 is a front view showing the mixing promoter in FIG. 2.

Next, FIG. 2 is a side view showing the chamber 20 in FIG. 1 in more detail, and FIG. 3 is a front view showing a mixing promoter 201 in FIG. 2. As shown in FIG. 2, the chamber 20 according to the present embodiment includes: a plurality of chamber bodies 200 aligned along the flow direction of the mixed gas 8; mixing promoters 201 each provided between the chamber bodies 200. Each chamber body 200 and each mixing promoter 201 are fastened to each other by fastening members 203 such as a bolt and a nut, for example.

The chamber body 200 according to the present embodiment is a tubular body to which the gas sensors 1 and the air-fuel ratio meter 6 can be attached. The number of the chamber bodies 200 may be changed depending on the number of the gas sensors 1 and the air fuel ratio meter 6 used.

The mixing promoters 201 according to the present embodiment are configured to promote the mixing of the first gas 3a and the second gas (the NO gas 5a, the air 5b, and the combustible gas 5c), and are provided in the pipe 2 (the chamber 20) on an upstream side of the gas sensor 1 in the flow direction of the first gas 3a (the mixed gas 8) and on a downstream side of the addition position of the second gas.

As shown in FIG. 3, each of the mixing promoters 201 according to the present embodiment is formed of a plate-shaped member having an opening 201a at substantially the center. The opening 201a according to the present embodiment has a rectangular shape extending so as to be long in the horizontal direction. However, the opening 201a may have other shapes such as a circle or a square, for example. The opening area of the opening 201a is narrower than an inner cross-sectional area of the chamber body 200. These areas are areas on a surface orthogonal to the flow direction of the mixed gas 8. That is, each mixing promoter 201 according to the present embodiment is a member for reducing a flow path cross-sectional area in the pipe as compared with the upstream and the downstream of the mixing promoter 201 in the flow direction of the first gas 3a (the mixed gas 8). In other words, each mixing promoter 201 according to the present embodiment is a member for narrowing the flow path. Immediately after the mixed gas 8 of the first gas and the second gas passes through the opening 201a, a vortex is generated in the mixed gas 8 on a back side of the mixing promoter 201, thereby promoting the mixing of the first gas 3a and the second gas (the NO gas 5a, the air 5b and the combustible gas 5c).

Although the present embodiment discloses that each mixing promoter 201 is provided between the chamber bodies 200 so as to correspond to each gas sensor 1, the mixing promoter 201 may be provided only at an introduction port of the most upstream chamber body 200 (an opening through which the mixed gas 8 is introduced). Although it discloses each mixing promoter 201 as being a different member from the chamber body 200, it may be integral with the chamber body 200. Further, the mixing promoter 201 is not limited to the plate-shaped member provided with the opening, and it may be other forms such as a rod-shaped member arranged to hinder the flow of the mixed gas 8, and a protrusion provided on an inner peripheral surface of each chamber body 200.

Figure 4:
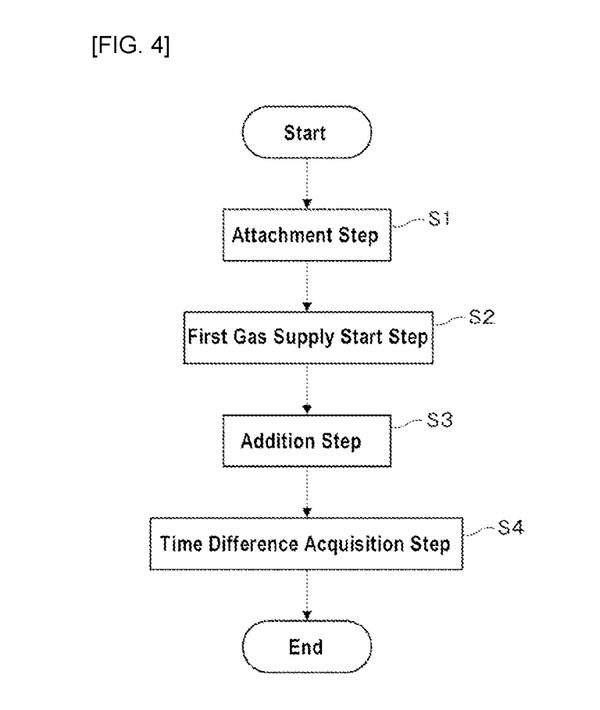
FIG. 4 is a flowchart showing a method for evaluating a response time of gas sensors using the response time evaluation apparatus shown in FIGS. 1 to 3.

Next, FIG. 4 is a flowchart showing a response time evaluation method for the gas sensors using the response time evaluation device shown in FIGS. 1 to 3. As shown in FIG. 4, the response time evaluation method for the gas sensor according to the present embodiment includes: an attachment step S1; a first gas supply start step S2; an addition step S3; and a time difference acquisition step S4.

In the attachment step S1, the gas sensors 1 are attached to the chamber 20 of the pipe 2. In the first gas supply start step S2, the supplying of the first gas 3a to the pipe 2 is started by the first gas supplier 3.

In the addition step S3, at least one of the first to third connecting pipes 51, 54, 57 is opened by at least one of the first to third connecting pipe on-off valves 52, 55, 58, and at least one of the NO gas 5a, the air 5b and the combustible gas 5c as the second gas is added to the first gas 3a in the pipe 2. When evaluating the response time of the NO output of the gas sensors 1, the NO gas 5a is added. Further, when evaluating the response time of the oxygen output of the gas sensors 1, at least one of the air 5b and the combustible gas 5c is added.

It is preferable that before opening at least one of the first to third connecting pipes 51, 54, 57 by at least one of the first to third connecting pipe on-off valves 52, 55, 58, at least one of the first supply control valve 502 and the first supply pipe on-off valve 503, the second supply control valve 532 and the second supply pipe on-off valve 533, as well as the third supply control valve 562 and the third supply pipe on-off valve 563 is opened to form the flow of the NO gas in the first supply pipe 501, and/or to form the flow of the air 5b in the second supply pipe 531, and/or to form the flow of the combustible gas 5c in the third supply pipe 561. Such previous forming of the flow can allow at least one of the NO gas 5a, the air 5b and the combustible gas 5c to be immediately added as the second gas to the first gas 3a in the pipe 2 when at least one of the first to third connecting pipes 51, 54, 57 is opened by at least one of the first to third connecting pipe on-off valves 52, 55, 58. When at least one of the first to third connecting pipes 51, 54, 57 is opened by at least one of the first to third connecting pipe on-off valves 52, 55, 58, the corresponding first to third supply pipe on-off valve 503, 533, 563 is closed.

In the time difference acquisition step S4, a time difference is acquired between a time point when at least one of the first to third connecting pipes 51, 54, 57 is opened by at least one of the first to third connecting pipe on-off valves 52, 55, 58, and a time point when the gas sensors detect components in the mixed gas 8 of the first and the second gases. This time difference can be evaluated as the response time of the gas sensors 1.

In the response time evaluation apparatus and method for the gas sensors according to the present embodiment, the second gas adding machine 5 includes: the second gas supply source 50, 53, 56; the connecting pipe 51, 54, 57 for connecting the supply source 50, 53, 56 to the pipe; and the connecting pipe on-off valve 52, 55, 58 for opening and closing the connecting pipe 51, 54, 57, so that the evaluation accuracy of response characteristic of the gas sensors 1 can be improved while simulating the actual use environment of the gas sensors 1.

Further, the connecting pipe on-off valve 52, 55, 58 according to the present embodiment is the electrically driven valve, so that the timing of opening/closing can be more accurately obtained and the evaluation accuracy of the response characteristic of the gas sensors 1 can be more reliably improved.

Furthermore, the connecting pipe on-off valve 52, 55, 58 according to the present embodiment are the solenoid valve, so that the timing of opening/closing can be more accurately acquired and the evaluation accuracy of the response characteristic of the gas sensors 1 can be further reliably improved.

Moreover, the distance between the addition position of the second gas and the gas sensor 1 according to the present embodiment is shorter than the distance between the addition position of the second gas and the first gas supplier 3, so that a quicker effect of the addition of the second gas at the position of the gas sensors 1 can be more reliably produced.

Further, the addition position of the second gas according to the present embodiment is on the downstream side of the cooler 4 in the flow direction of the first gas 3a, so that the quicker effect of the addition of the second gas at the position of the gas sensors 1 can be more reliably produced.

Furthermore, when the connecting pipe 51, 54, 57 is closed by the connecting pipe on-off valve 52, 55, 58, it is configured to be capable of forming the flow of the second gas in the supply pipe 501, 531, 561, so that the second gas can be added immediately when the connecting pipe on-off valve 52, 55, 58 is opened, and the evaluation accuracy of the response characteristic of the gas sensors 1 can be more reliably improved.

Further, the supply source 50, 53, 56 is provided with the supply pipe on-off valve 503, 533, 563 disposed on the downstream side of the connection position of the connecting pipe 51, 54, 57 to the supply pipe 501, 531, 561 in the flow direction of the second gas, so that when the connecting pipe on-off valve 52, 55, 58 is opened, the supply pipe on-off valve 503, 533, 563 is closed, whereby the second gas can be more quickly supplied to the connecting pipe 51, 54, 57, and the evaluation accuracy of the response characteristic of the gas sensors 1 can be more reliably improved.

Further, the mixing promoters 201 for promoting the mixing of the first and second gases is provided on the upstream side of the gas sensors 1 in the flow direction of the first gas 3a and on the downstream side of the addition position of the second gas, so that it is possible to avoid occurrence of detection delay of the gas sensors 1 due to insufficient mixing of the first and second gases and to improve the evaluation accuracy of the response characteristic of the gas sensors 1 more reliably.

Furthermore, each mixing promoter 201 is a member for reducing the flow path cross-sectional area in the pipe as compared with the upstream and downstream of the mixing promoter 201 in the flow direction of the first gas 3*a*, so that it is possible to generate a vortex in the mixed gas 8 of the first and the second gases and to promote the mixing of the first gas 3*a* and the second gas more reliably.

DESCRIPTION OF REFERENCE NUMERALS

1 gas sensor
2 pipe
201 mixing promoter
3 first gas supplier
4 cooler
5 second gas adding machine
5*a* NO gas (second gas)
5*b* air (second gas)
5*c* combustible gas (second gas)
50 NO gas supply source (supply source)
500 NO gas supply body (supply source body)
501 first supply pipe (supply pipe)
503 first supply pipe on-off valve (supply pipe on-off valve)
51 first connecting pipe (connecting pipe)
52 first connecting pipe on-off valve (connecting pipe on-off valve)
53 second air supply source (supply source)
530 second air supply source body (supply source body)
531 second supply pipe (supply pipe)
533 second supply pipe on-off valve (supply pipe on-off valve)
54 second connecting pipe (connecting pipe)
55 second connecting pipe on-off valve (connecting pipe on-off valve)
56 second combustible gas supply source (supply source)
560 second combustible gas source body (supply source body)
561 third supply pipe (supply pipe)
563 third supply pipe on-off valve (supply pipe on-off valve)
57 third connecting pipe (connecting pipe)
58 third connecting pipe on-off valve (connecting pipe on-off valve)
8 mixed gas

What is claimed is:

1. An apparatus for evaluating a response time of gas sensors, comprising:
   a pipe;
   a first gas supplier configured to supply a first gas to the pipe;
   a second gas adding machine configured to add a second gas to the first gas in the pipe; and
   gas sensors configured to detect components in a mixed gas of the first gas and the second gas, each of the gas sensors being attached to the pipe on a downstream side of an addition position of the second gas in a flow direction of the first gas,
   wherein the second gas adding machine comprises: a supply source of the second gas; a connecting pipe for connecting the supply source to the pipe; and a connecting pipe on-off valve for opening and closing the connecting pipe, and
   wherein the supply source comprises: a supply source body for supplying the second gas; and a supply pipe to which the second gas is supplied from the supply source body and the connecting pipe is connected, and wherein the supply source is configured to be capable of forming a flow of the second gas in the supply pipe when the connecting pipe is closed by the connecting pipe on-off valve.

2. The apparatus for evaluating a response time of gas sensors according to claim 1, wherein the connecting pipe on-off valve is an electrically driven valve.

3. The apparatus for evaluating a response time of gas sensors according to claim 2, wherein the connecting pipe on-off valve is an electromagnetic valve.

4. The apparatus for evaluating a response time of gas sensors according to claim 1, wherein a distance between an addition position of the second gas and the gas sensor is shorter than a distance between the addition position of the second gas and the first gas supplier.

5. The apparatus for evaluating a response time of gas sensors according to claim 1,
   wherein the first gas is a combustion gas in which a combustible gas has been burned;
   wherein the apparatus further comprises a cooler for cooling the first gas; and
   wherein the addition position of the second gas is on a downstream side of the cooler in the flow direction of the first gas.

6. The apparatus for evaluating a response time of gas sensors according to claim 1, wherein the supply source further comprises a supply pipe on-off valve for opening and closing the supply pipe, the supply pipe on-off valve being arranged on a downstream side of a connection position of the connecting pipe to the supply pipe in the flow direction of the second gas.

7. The apparatus for evaluating a response time of gas sensors according to claim 1, further comprising mixing promoters for promoting the mixing of the first gas and the second gas, the mixing promoters being provided in the pipe on an upstream side of the gas sensors and on a downstream side of the addition position of the second gas in the flow direction of the first gas.

8. The apparatus for evaluating a response time of gas sensors according to claim 7, wherein each of the mixing promoters is a member for reducing a flow path cross-sectional area in the pipe as compared with the upstream and downstream of the mixing promoter in the flow direction of the first gas.

9. A gas sensor response time evaluating method for evaluating the response time of the gas sensors using the apparatus according to claim 1, the method comprising:
   an attachment step of attaching the gas sensors to the pipe;
   a first gas supply start step of starting supply of the first gas to the pipe by the first gas supplier;
   an addition step of opening the connecting pipe by the connecting pipe on-off valve and adding the second gas to the first gas in the pipe; and
   a time difference acquisition step of acquiring a time difference between a time point when the connecting pipe is opened by the connecting pipe on-off valve and a time point when the gas sensors detect components in the mixed gas of the first and second gases.

10. The gas sensor response time evaluating method according to claim 9, wherein the flow of the second gas is formed in the supply pipe before the connecting pipe is opened by the connecting pipe on-off valve.

11. The gas sensor response time evaluating method according to claim 9,
   wherein the supply source further comprises a supply pipe on-off valve for opening and closing the supply pipe, the supply pipe on-off valve being arranged on a downstream side of a connection position of the connecting pipe to the supply pipe in the flow direction of the second gas, and wherein the flow of the second gas is formed in the supply pipe before the connecting pipe is opened by the connecting pipe on-off valve.

12. An apparatus for evaluating a response time of gas sensors, comprising:

a pipe;

a first gas supplier configured to supply a first gas to the pipe;

a second gas adding machine configured to add a second gas to the first gas in the pipe; and gas sensors configured to detect components in a mixed gas of the first gas and the second gas, each of the gas sensors being attached to the pipe on a downstream side of an addition position of the second gas in a flow direction of the first gas, wherein the second gas adding machine comprises: a supply source of the second gas; a connecting pipe for connecting the supply source to the pipe; and a connecting pipe on-off valve for opening and closing the connecting pipe, and wherein the response time of the gas sensors is determined based on a time difference between a time point when the connecting pipe is opened by the connecting pipe on-off valve and a time point when the gas sensors detect components in a mixed gas of the first and second gases.

* * * * *